United States Patent
Wakabayashi et al.

(10) Patent No.: US 7,400,513 B2
(45) Date of Patent: Jul. 15, 2008

(54) CONDUCTIVE PRINTED BOARD, MULTICORE CABLE AND ULTRASONIC PROBE USING THE SAME

(75) Inventors: Takashi Wakabayashi, Saitama (JP); Yasuo Shimizu, Saitama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 287 days.

(21) Appl. No.: 10/827,885

(22) Filed: Apr. 20, 2004

(65) Prior Publication Data

US 2004/0262030 A1 Dec. 30, 2004

(30) Foreign Application Priority Data

Apr. 22, 2003 (JP) .............................. 2003-116649
Apr. 24, 2003 (JP) .............................. 2003-120568

(51) Int. Cl.
*H05K 7/10* (2006.01)
*H05K 7/12* (2006.01)

(52) U.S. Cl. ..................... 361/770; 361/749; 174/254

(58) Field of Classification Search .............. 174/254; 361/749; 310/330–337
See application file for complete search history.

(56) References Cited

U.S. PATENT DOCUMENTS

| | | | | |
|---|---|---|---|---|
| 4,701,659 A | * | 10/1987 | Fujii et al. | ............... 310/334 |
| 5,931,684 A | * | 8/1999 | Obendorf et al. | ............... 439/67 |
| 6,100,626 A | * | 8/2000 | Frey et al. | ............... 310/334 |
| 6,201,689 B1 | * | 3/2001 | Miyasyo | ............... 361/681 |
| 6,541,896 B1 | * | 4/2003 | Piel et al. | ............... 310/334 |
| 7,090,505 B2 | * | 8/2006 | Herve | ............... 439/67 |

FOREIGN PATENT DOCUMENTS

JP 2003-102732 4/2003

* cited by examiner

*Primary Examiner*—Tuan T Dinh
(74) *Attorney, Agent, or Firm*—Scott D. Wofsy; Edwards Angell Palmer & Dodge LLP

(57) ABSTRACT

The present invention relates to a conductive printed board which can be used as a common part and therefore offers high productivity, and an ultrasonic probe which uses this conductive printed board. In a conductive printed board having terminals which are provided either in a contiguous manner or at a defined array spacing, and are connected to conduction paths, terminals connected to the terminals and spaced with different array spacing from the defined array spacing are provided on the ends. The conductive printed board is a flexible printed board, and a plurality of piezo elements having excitation electrodes on both main faces are lined up at the defined array spacing. If the terminals are widely spaced, the object can connect as-is to the other terminals, and if the terminals are spaced narrowly, then the portion with the other terminals can be removed, allowing the terminals to be connected. Moreover, the present invention relates to a multicore cable for which the weight and diameter of the multicore cable are reduced, thus facilitating multifunctionality, and to an ultrasonic probe with excellent operability and functionality which uses this multicore cable. The multicore cable is constructed by winding a flexible printed board containing signal conductors helically within a flexible outer jacket.

6 Claims, 8 Drawing Sheets

CONDUCTIVE PRINTED BOARD, MULTICORE CABLE AND ULTRASONIC PROBE USING THE SAME

BACKGROUND OF THE INVENTION

1. Field of the Invention

The present invention relates to a conductive printed board and an ultrasonic probe using this conductive printed board, and more particularly to an ultrasonic probe wherein productivity is improved by enabling the use of the conductive printed board as a common part.

2. Description of the Related Art

An ultrasonic probe is used in, for example, ultrasonic diagnostic equipment for medical use, as a transducer which transmits and receives ultrasonic waves. One example of such an ultrasonic probe is an array type ultrasonic probe, in which a plurality of piezoelectric elements having electrodes on both the faces are arranged in a line, and generally the electrodes are led out by a conductive printed board. From recently there are various types of ultrasonic probes distinguished by the number of piezoelectric elements and their array pitch, leading to a call for communization (use as a common part) of the conductive printed board.

FIG. 7A and FIG. 7B show a conventional example of an ultrasonic probe, wherein FIG. 7A is a partially cutaway front view and FIG. 7B is a side view.

As shown in FIG. 7A and FIG. 7B, in conventional ultrasonic probes, a plurality of piezoelectric elements 42 which have excitation electrodes 41a and 41b on both major faces are arranged in a line with defined array spacing (pitch interval d) upon a backing material 43, and connected to an excitation electrode 41a provided on the bottom surface of the piezoelectric elements 42 by conductive wires 45 of a flexible printed board 44. Furthermore, the excitation electrodes 41b on the top surfaces of the piezoelectric elements 42 are connected commonly by a conductor, for example, and are thereby connected electrically to other conductive wires 45 of the flexible printed board 44. In addition, in the case of medical use, an acoustic matching layer not shown in the diagram (to achieve acoustic matching with a living organism), and if needed an acoustic lens (for changing emitted ultrasonic waves into a narrow beam), are provided on the piezoelectric elements 42.

Normally, as shown in FIG. 7B, a piezoelectric plate comprising the excitation electrodes 41a and 41b and the piezoelectric element 42, is connected to the flexible printed board 44, for example, and fixedly secured to the backing material 43. As shown in FIG. 8A and FIG. 8B, the flexible printed board 44 has a plurality of fine conduction paths 45 arranged in parallel or other directions. The conduction paths 45 shown in FIG. 8A and FIG. 8B connect to contiguous terminals 46 provided at the tips of the conduction paths, which are later divided (see FIG. 8A). Alternatively, the conduction paths 45 are connected to terminals 46 which are arranged with the same array spacing d as the piezoelectric elements 42 (see FIG. 8B). Cuttings 47 are then made in the piezoelectric elements 42 from the top of the acoustic matching layer to the backing material 43 thereby severing the piezoelectric elements 42 and dividing the piezoelectric elements 42 into individual piezoelectric elements 42 and terminals 46 arranged at the defined array spacing d (see FIG. 7A).

However, in some cases, with such conventional ultrasonic probes, as shown in FIG. 9A and FIG. 9B, a different array spacing d may be used (using $d_2$ instead of $d_1$) for the same number of piezoelectric elements 42. Therefore, it is necessary to separately design a different flexible printed board for use with each of the different array spacings ($d_1$, $d_2$). Consequently, the flexible printed board 44 cannot be used as a common part, which presents a particular problem in that the more types of ultrasonic probes there are, the more inventory is required, which lowers productivity.

The present invention also relates to a multicore cable and an ultrasonic probe using the multicore cable, and relates particularly to a multicore cable which maintains flexibility.

As mentioned above, an ultrasonic probe is a transducer which transmits and receives ultrasonic waves, used for example in ultrasonic diagnostic equipment for medical use. Normally, an ultrasonic probe comprises a probe main body including a plurality of piezoelectric element groups arranged in a line, and a multicore cable which connects the probe main body electrically to the main body of the diagnostic tool (see Japanese Laid-Open Patent Publication No. 2003-102732, for example). Recently, for medical and operational reasons, there is a call for smaller and lighter ultrasonic probes.

FIG. 10 and FIG. 11A to FIG. 11C show a conventional example of such an ultrasonic probe, wherein FIG. 10 is a sectional view of the ultrasonic probe, FIG. 11A is a front view of the probe main body, FIG. 11B is a side view thereof, and FIG. 11C is a partially cut away back view thereof.

Normally, as shown in FIG. 10, the ultrasonic probe comprises a probe main body 61 and a multicore cable 62, and the probe main body 61 is housed within a case 63. Also, a construction is used in which piezoelectric element groups 65 arranged in a line upon a backing material 64 are exposed through an opening in the case 63. Normally, an acoustic matching layer and an acoustic lens (neither shown in the drawing) are provided on the piezoelectric element groups 65, and the piezoelectric element groups 65, on the major faces of which are provided excitation electrodes 65a and 65b, are connected to the back surface of the backing material 64 by means of a flexible printed board 66, for example.

Furthermore, as shown in FIG. 11A to FIG. 11C, the flexible printed board 66 comprises a resin film 66a in which a plurality of signal conductors 67 are provided. The excitation electrodes 65a and 65b of the piezoelectric element groups 65 are bonded to the signal conductors 67 by solder or the like as shown in FIG. 11A, to establish an electrical connection. Moreover, the excitation electrodes 65b on the bottom surface side (the backing material 64 side) of the piezoelectric element groups 65, and the signal conductors 67 of the flexible printed board 66 are connected. Also, the top surface side (transducer side) of the piezoelectric element groups 65 is connected commonly by conductors (not shown), for example, to form a grounding surface, which is connected to a grounding wire of the flexible printed board 66.

In addition, as shown in FIG. 12A, a multicore cable 72 comprises a plurality of coaxial cables 73 (for example 128 cables) sheathed within an outer jacket 70. The coaxial cables 73, as shown in FIG. 12B, have a four-layered construction comprising a central conductor 73a, a first insulating material 73b, a braided shield 73c and a second insulating material 73d, layered concentrically. The central conductor 73a of each coaxial cable 73 is connected to a signal conductor 67 on the flexible printed board 66, and the braided shield 73c is connected to another signal conductor 67 for grounding the flexible printed board 66. In addition, the outer jacket 70 is made of a resin or the like, which demonstrates flexibility. Normally, a shielding material 71 is provided on the inner surface of the outer jacket 70, collectively shielding the plurality of coaxial cables 73.

However, because the conventional ultrasonic probes as described above use four-layered coaxial cables, it is not possible to reduce the diameter of the multicore cable 72.

Furthermore, the terminals 68 of the signal conductors provided on the flexible printed board 66 (see FIG. 11C) cannot normally be provided at narrower spacing than the diameter of the coaxial cables 73, which impedes miniaturization. Accordingly, there is a problem in that the greater the number of piezoelectric elements, that is the greater the number of channels, the larger the diameter of the multicore cable 72, which prevents miniaturization.

Specifically, when an ultrasonic probe for medical use is to be inserted into a body cavity, the multicore cable 72 cannot have a large diameter. Consequently, increasing the number of channels, for example in order to improve resolution of the ultrasonic probe, is problematic. In addition, there is a problem in that it is difficult to integrate a medical catheter with an ultrasonic probe, for example, preventing multifunctionality from being achieved. Furthermore, because an ultrasonic probe according to the conventional example is constructed with bundled coaxial cables, there is a problem in that such an ultrasonic probe is heavy, and therefore operability is poor.

SUMMARY OF THE INVENTION

An object of the present invention is to provide a conductive printed board which can be used as a common part and therefore offers high productivity, and an ultrasonic probe which uses this conductive printed board.

The conductive printed board according to the present invention is connected to terminals (hereafter called as the first terminals), which are provided either in a contiguous manner or at a defined array spacing, and are connected to conduction paths on a flexible printed board, and at the ends of the first terminals are provided terminals (hereafter called as the second terminals) spaced with different spacing from that of the first terminals.

As a result, by using wider spacing for the second terminals than that of the first terminals, if the terminals of the object to which the printed board is to be connected are widely spaced, the object can connect as-is to the second terminals, and if the terminals of the object to which the printed board is to be connected are spaced narrowly, then the portion with the second terminals can be removed, allowing the terminals of the object to be connected, to be connected directly to the first terminals.

Furthermore, because the conductive printed board of the present invention is made of a flexible printed board, it is most suitable for connecting objects that must undergo bending and the like.

Moreover, with the ultrasonic probe of the present invention, the excitation electrodes of the plurality of piezoelectric elements arranged in a line with defined array spacing are connected to a conductive printed board having either the first terminals or the second terminals, for example the flexible printed board, to constitute the ultrasonic probe. As a result, the conductive printed board can be used as a common part, which improves the productivity of the ultrasonic probe.

Furthermore, another object of the present invention is to provide a multicore cable which is lightweight and small in diameter, and an ultrasonic probe using such a multicore cable.

In particular, in the present invention, the multicore cable is constructed by winding a flexible printed board containing signal conductors helically within a flexible outer jacket. As a result, this flexible printed board can be used in place of coaxial cables, and because the flexible printed board is disposed helically within the outer jacket, the weight and diameter of the multicore cable can be reduced. By disposing the flexible printed board helically within the outer jacket, it is possible to leave a cavity in the central region of the multicore cable, providing room for inserting a catheter, for example, which facilitates a multifunction ultrasonic probe.

Furthermore, with the multicore cable of the present invention, the outer jacket has a shielding action which shields from external noise, which makes the multicore cable of the present invention particularly useful as a cable for electrical equipment.

In addition, in the present invention, because the ultrasonic probe is constructed by electrically connecting between the excitation electrodes of the piezoelectric element groups of which a plurality are arranged in a line to constitute the probe main body, and the signal conductors of the flexible printed board, the effects of the multicore cable of the present invention are further enhanced, so that an ultrasonic probe with excellent operability and functionality is obtained.

BRIEF DESCRIPTION OF THE DRAWINGS

FIG. 5A and FIG. 5B are partially cut away views showing an embodiment of a multicore cable according to the present invention, wherein FIG. 5A is a partially cut away front view of a probe main body and FIG. 5B is a partially cut away enlarged side view.

FIG. 7A and FIG. 7B are diagrams for explaining a conventional example of an ultrasonic probe, wherein FIG. 7A is a partially cut away front view of the ultrasonic probe and FIG. 7B is a side view thereof.

FIG. 8A and FIG. 8B are front views showing a conventional example of an ultrasonic probe, particularly a flexible printed board of an ultrasonic probe, wherein FIG. 8A shows an example in which the conduction paths of the flexible printed board are connected at their ends, and FIG. 8B shows an example in which the ends of the conduction paths are already separated.

FIG. 9A and FIG. 9B are front views showing a conventional example of an ultrasonic probe, particularly a flexible printed board of an ultrasonic probe, wherein FIG. 9A shows a case where wide spacing is employed for the terminals, and FIG. 9B shows a case where narrow spacing is employed.

FIG. 11A to FIG. 11C are diagrams showing a conventional example of a probe main body, wherein FIG. 11A is a front view, FIG. 11B is a side view, and FIG. 11C is a back view thereof.

DETAILED DESCRIPTION OF THE INVENTION

First Embodiment

Figure 1:
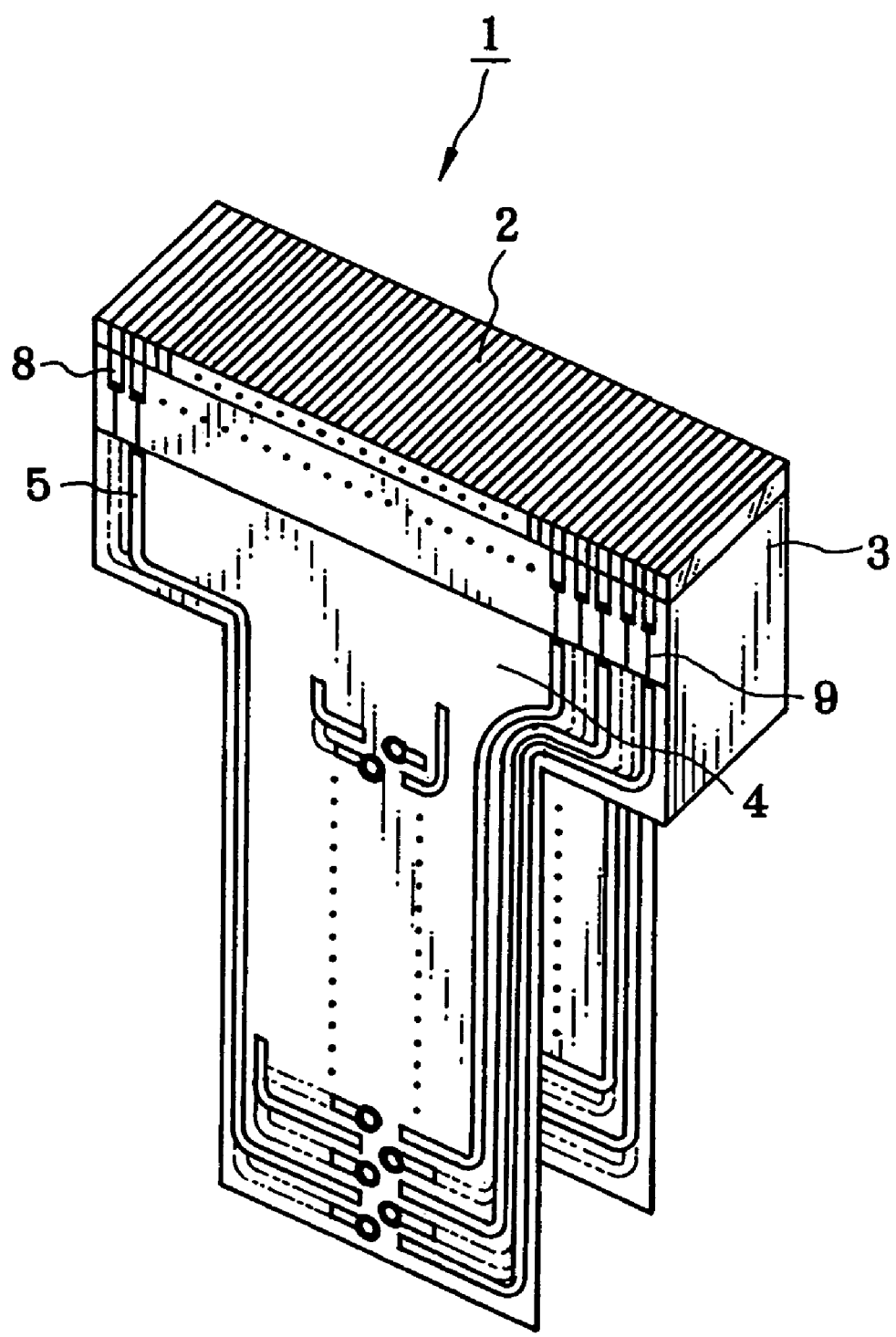
FIG. 1 is a perspective view showing an ultrasonic probe to which the conductive printed board of the present invention is applied.

FIG. 1 is a partially cut away front view describing an embodiment of an ultrasonic probe according to the present invention, showing in particular a partially cut away front view of a conductive printed board (flexible printed board).

As shown in FIG. 1, in the ultrasonic probe 1 of the present invention, a plurality of piezoelectric elements 2 having excitation electrodes on both major faces are arranged in a line on a backing material 3, and are connected to excitation electrodes by a conductive printed board, here a flexible printed board 4.

Figure 2:
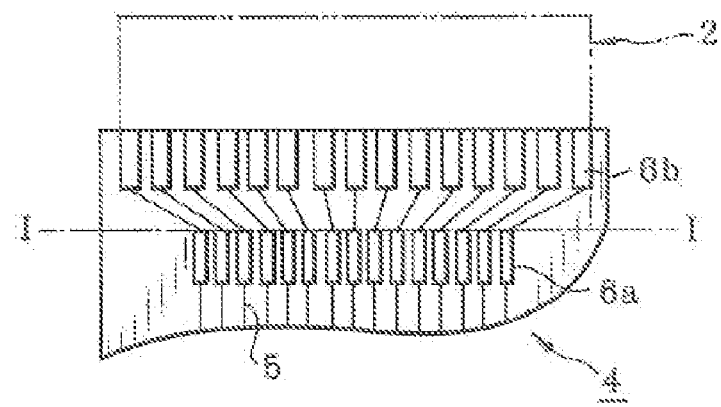
FIG. 2 is a front view showing an ultrasonic probe to which a first embodiment of the conductive printed board of the present invention is applied, particularly a flexible printed board.

As shown in FIG. 2, the construction of the flexible printed board 4 is such that first terminals 6a are connected to a plurality of conduction paths 5, and second terminals 6b are further connected to the ends of the first terminals 6a via the conduction paths 5. Here, the number of first terminals 6a and second terminals 6b is the same. Furthermore, because the array spacing of the second terminals 6b is wider than that of the first terminals 6a, the first terminals 6a have smaller array spacing, while the second terminals 6b have larger array spacing.

With such a flexible printed board 4, if the piezoelectric elements 2 are widely spaced, then the piezoelectric plate is connected to the tip side of the second terminals 6b. Furthermore, if the piezoelectric elements 2 are narrowly spaced, then the second terminals 6b are cut out and removed along the line I-I, leaving the first terminals 6a, and the piezoelectric plate is connected to the first terminals 6a. Cuttings are then made in the piezoelectric plate through an acoustic matching layer (not shown) with defined spacing, to obtain the individual piezoelectric elements 2.

Figure 3:
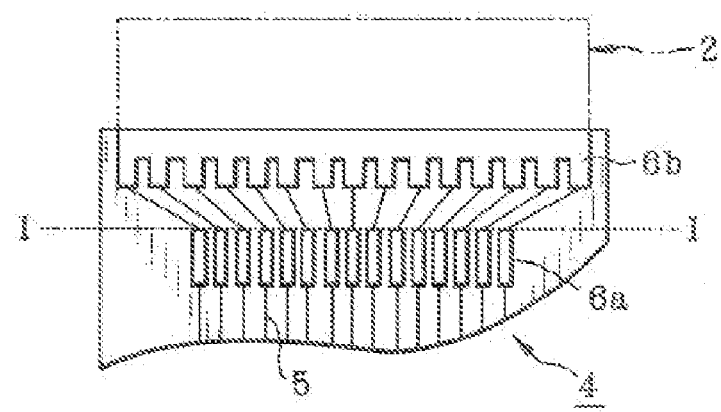
FIG. 3 is a front view showing an ultrasonic probe, being another example of the first embodiment of the conductive printed board of the present invention, particularly a flexible printed board.

By employing such a configuration, even when the piezoelectric elements 2 are spaced differently, by simply excising the portion which includes the second terminals 6b along the line I-I, and removing it, the flexible printed board 4 can be used as a common part with different terminal spacing. Accordingly, the productivity of the flexible printed board 4 is improved. Here, the second terminals 6b are formed by dividing the terminals with defined spacing, but as shown in FIG. 2 and FIG. 3, the terminals may be formed in a contiguous manner, and cut together with the piezoelectric elements 2.

Second Embodiment

Figure 4:
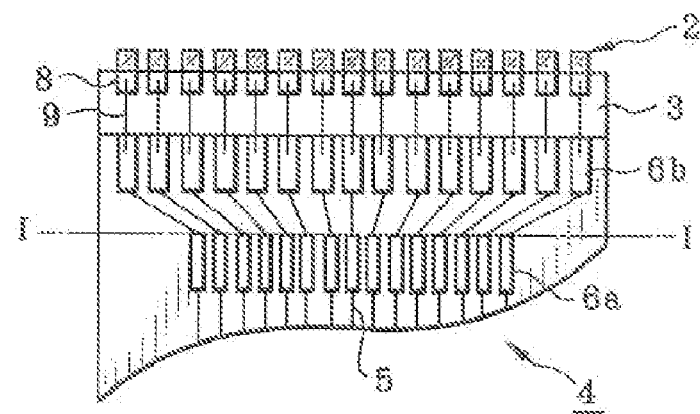
FIG. 4 is a front view showing an ultrasonic probe, being a second embodiment of the conductive printed board of the present invention.

FIG. 4 is a front view showing an ultrasonic probe according to a second embodiment of the present invention.

In the first embodiment described above, the excitation electrodes of the piezoelectric elements are connected directly via the flexible printed board 4, but in this embodiment the excitation electrodes are connected in an indirect manner. That is, copper foil 8 or the like is disposed between the piezoelectric elements 2 and the backing material 3. In this case also, the terminals are cut together with the piezoelectric plate, and the copper foil 8 is led out from the individual piezoelectric elements 2. The copper foil 8 is then connected by gold wire 9 or the like to the first terminals 6a or second terminals 6b of the flexible printed board 4 affixed to the front surface of the backing material 3.

With such a configuration, as with the first embodiment described above, by choosing between the first terminals 6a and the second terminals 6b as appropriate, the same flexible printed board 4 can be used as a common part with differently spaced piezoelectric elements 2.

While the flexible printed board 4 remains attached to the piezoelectric plate and the backing material 3, it is difficult to perform cutting using the cutting equipment such as a dicing saw. Furthermore, if a convex shaped piezoelectric plate is used, the flexible printed board 4 acquires bulk and becomes difficult to bend. For such reasons, the excitation electrodes are primarily led out by the copper foil 8 or the like. Furthermore, in this example the conductive printed board is a flexible printed board 4, but a rigid printed board made of a glass epoxy material, for example, may also be used. Also, this example has two rows of terminals, but three or more may be provided.

Embodiment 3

Figure 5A:
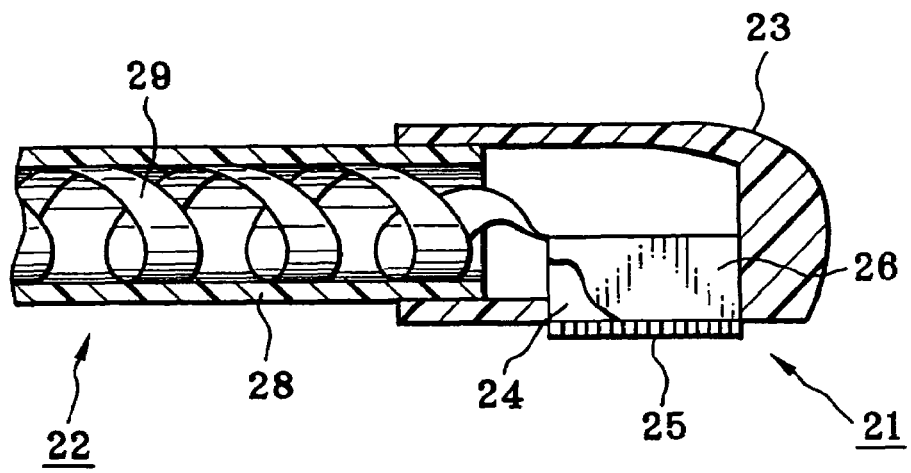
Figure 5B:
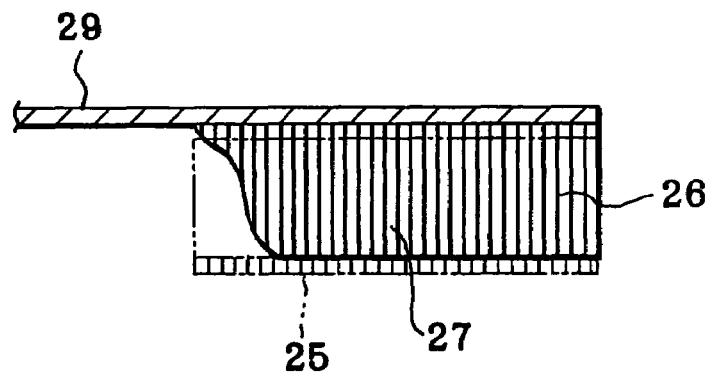
Figure 11A:
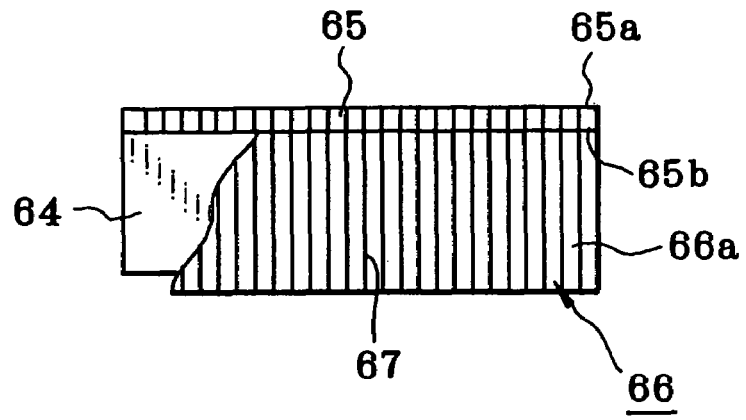
Figure 11B:
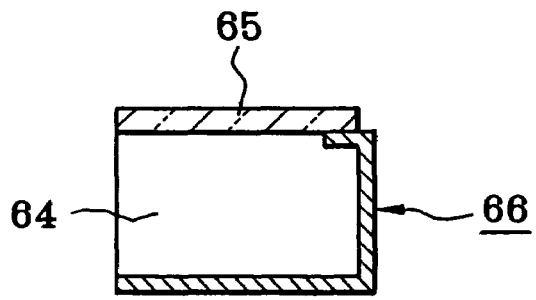
Figure 11C:
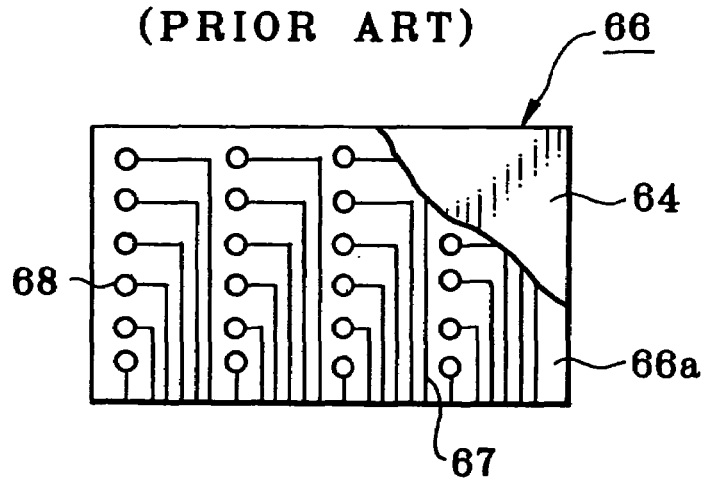

FIG. 5A and FIG. 5B are sectional views showing an embodiment of an ultrasonic probe using a multicore cable of the present invention. As shown in FIG. 5A, this ultrasonic probe comprises a probe main body 21 housed within a casing 23 and having terminals 68 (see FIG. 11C) on the rear surface thereof, and a multicore cable 22. The multicore cable 22 is provided with a flexible printed board for transmission 29 wound in a helix within the inner peripheral surface of an outer jacket 28. Furthermore, the flexible printed board for transmission 29 has signal conductors (not shown) provided in a resin film as well as terminals lined up over the length and breadth of one end thereof The flexible printed board for transmission 29 and the terminals 68 (see FIG. 11C) of the probe main body 21 are joined by solder or the like to establish an electrical connection. A shielding material such as a braided mesh or film may be provided on the inner peripheral surface of each outer jacket 28.

Figure 12A:
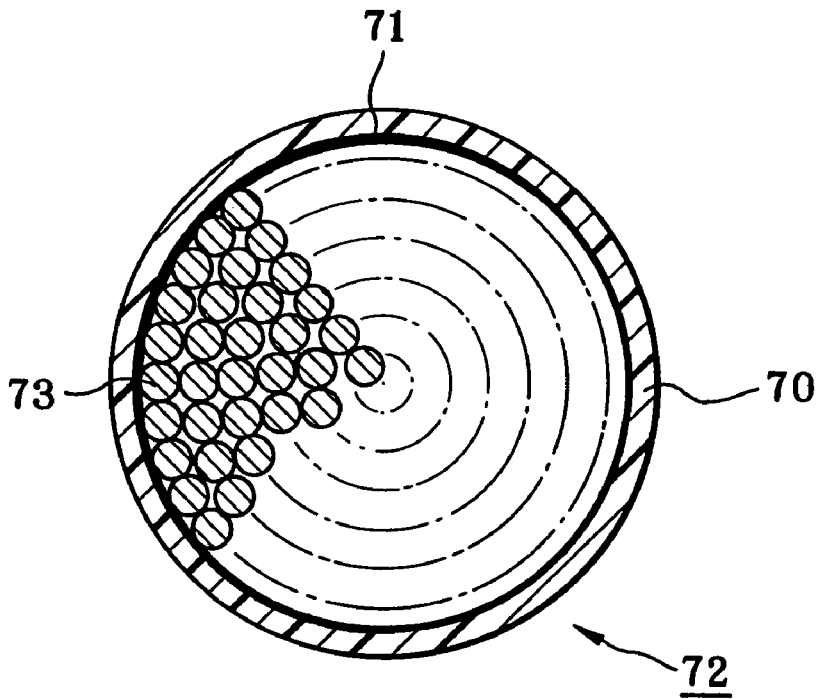
FIG. 12A and FIG. 12B are sectional views showing a multicore cable (FIG. 12A) and coaxial cable (FIG. 12B) as applied to a conventional ultrasonic probe.
Figure 12B:
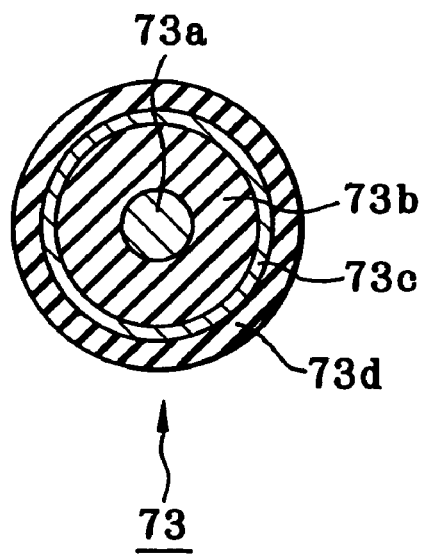

By employing such a configuration, in the present invention, because the flexible printed board for transmission 29 is housed within the outer jacket 28 in a helically wound state, then the multicore cable 22 can have a smaller diameter and less weight for a higher numbers of channels, compared to the case where coaxial cables 73 are bundled together (see also FIG. 12A).

Figure 6:
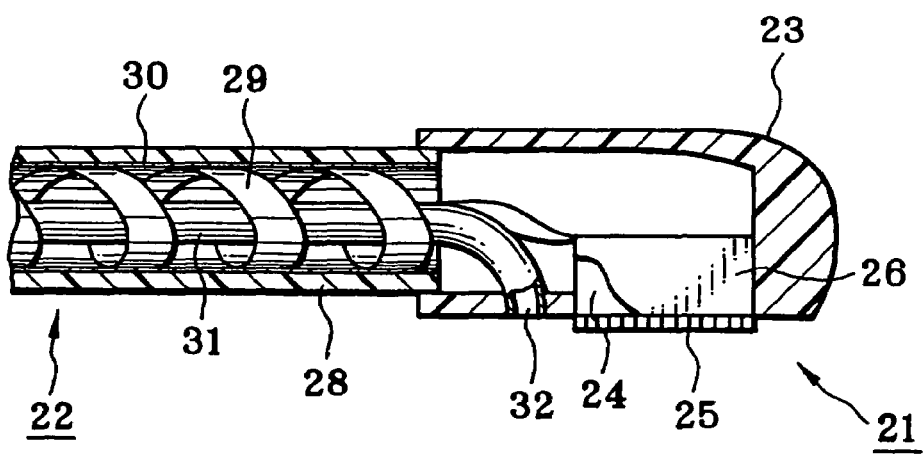
FIG. 6 is a sectional view showing an example of an application of the multicore cable of the present invention to an ultrasonic probe.
Figure 7A:
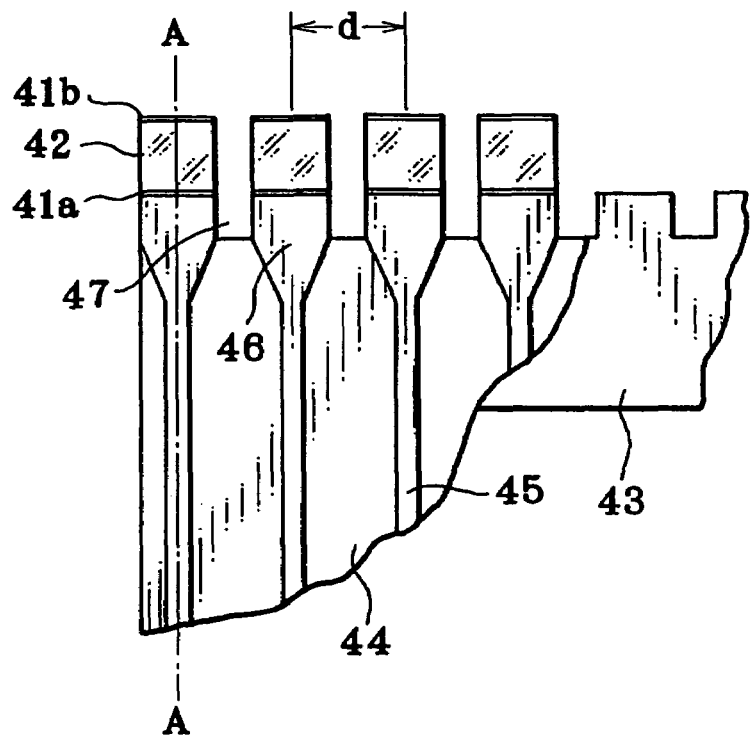
Figure 7B:
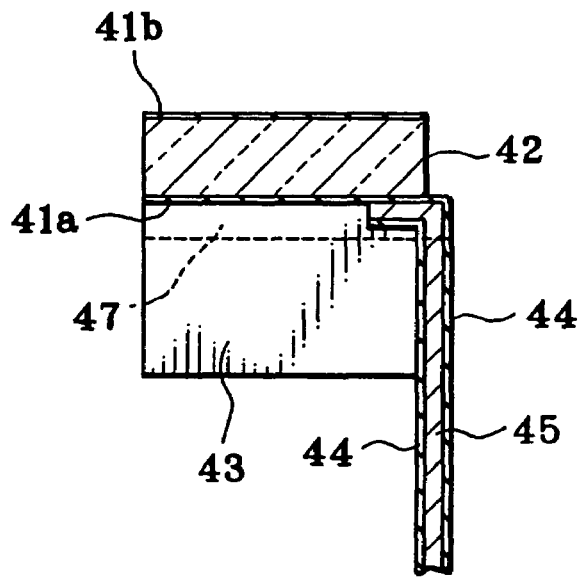
Figure 8A:
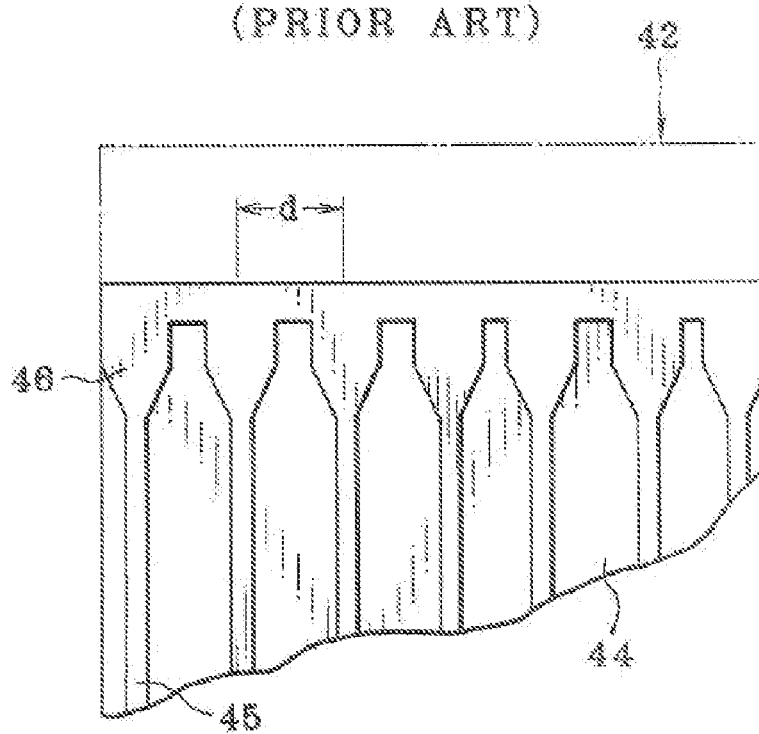
Figure 8B:
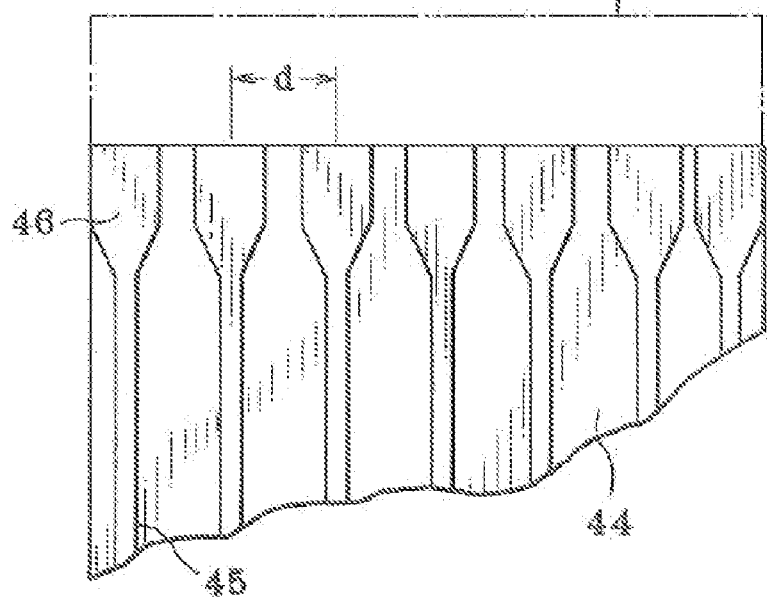
Figure 9A:
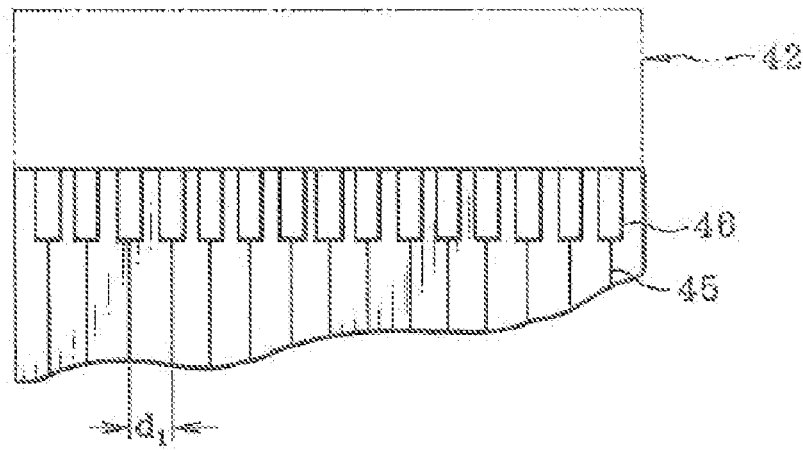
Figure 9B:
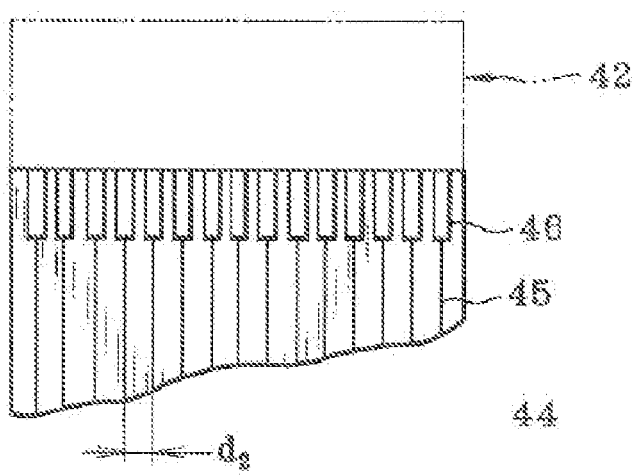
Figure 10:
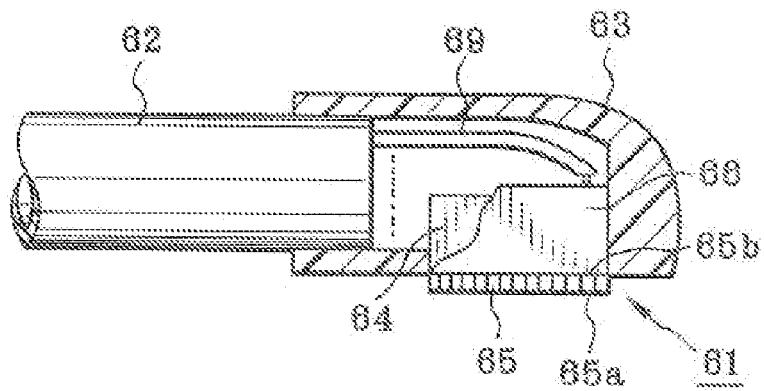
FIG. 10 is a partially cut away front view showing a conventional example of an ultrasonic probe.

Also, because the flexible printed board for transmission 29 is housed within the outer jacket 28 in a helically wound state, a cavity is left on the inner side of the multicore cable 22. Therefore for example, as shown in FIG. 6, it is possible to insert a medical catheter 31 for example into this cavity, and expose a forceps insertion opening 32 on the case surface of the probe main body. As a result, it is possible, while performing ultrasonic diagnostics of a target area, to also remove a portion of an organ using forceps, for example, which contributes overall to the multifunctionality of the ultrasonic probe.

In the example above, the terminals 68 (see FIG. 11C) are provided by extending the flexible printed board 26 from the back surface of the probe main body 21. However, for example the flexible printed board for transmission 29 may also be connected to the probe main body 21 after connecting a hard printed board using a connector. Any desired configuration can be used to connect the probe main body 21 and the flexible printed board for transmission 29.

Furthermore, in the construction of the flexible printed board for transmission 29, signal conductors are provided in a resin film. However a flexible flat cable, for example, which has multiple signal conductors, may also be used. Essentially any type of flat transmission medium which is capable of being wound helically may be used. Also, the multicore cable 22 was used in an ultrasonic probe, but the present invention is not limited to this application, and can also be applied to the connections in electronic components and electrical equipment as well.

What is claimed is:

1. An ultrasonic probe comprising:
   I) a conductive printed board having:
      a) a first set of terminals provided on the conductive printed board with a first lateral array spacing, the first terminals being connected to conduction paths; and
      b) a second set of terminals provided on the conductive printed board with a second lateral array spacing, the second lateral array spacing being greater than the first lateral array spacing, the second terminals being connected to ends of respective first terminals via respective conduction paths, thereby allowing severing and removal along a predetermined line of the second set of terminals, to alter terminal spacing of the conductive printed board, allowing the conductive printed board to be used as a universal part, having selectable lateral terminal spacing; and
   II) a plurality of piezo elements having excitation electrodes on both main faces thereof, and arranged with a defined spacing therebetween, said excitation electrodes being selectively connected to either the first set or the second set of terminals provided on the conductive printed board.

2. The ultrasonic probe according to claim 1, wherein said conductive printed board is a flexible printed board.

3. The ultrasonic probe according to claim 1, wherein said conductive printed board is a rigid printed board made of glass epoxy material.

4. The ultrasonic probe according to claim 1, wherein said terminals are in three or more rows.

5. A method of manufacturing an ultrasonic probe, board comprising the steps of:
   forming a first set of terminals connected to respective conduction paths on a conductive printed board, the first set of terminals having a first lateral array spacing;
   forming a second set of terminals on the conductive printed board with a second lateral array spacing, the second lateral array spacing being greater than the first lateral array spacing, the second terminals being connected to ends of respective first terminals via respective conduction paths, thereby allowing severing and removal along a predetermined line of the second set of terminals, to alter terminal spacing of the conductive printed board, allowing the conductive printed board to be used as a universal part, having selectable lateral terminal spacing; and
   selectively attaching a plurality of piezo elements having excitation electrodes on both main faces thereof, and arranged with a defined spacing therebetween, to either the first set or the second set of terminals provided on the conductive printed board.

6. An ultrasonic probe, comprising:
   I) a conductive printed board having:
      a) a first set of terminals provided on the conductive printed board with a first lateral array spacing, the first terminals being connected to a first set of conduction paths and a second set of conduction paths; and
      b) a second set of terminals provided on the conductive printed board with a second lateral array spacing, the second lateral array spacing being greater than the first lateral array spacing, the second terminals being connected to ends of respective first terminals via the second set of conduction paths, thereby allowing severing and removal along a predetermined line of the second set of terminals, to alter terminal spacing of the conductive printed board, allowing the conductive printed board to be used as a universal part, having selectable lateral terminal spacing; and
   II) a plurality of piezo elements having excitation electrodes on both main faces thereof, and arranged with a defined spacing therebetween, said excitation electrodes being selectively connected to either the first set or the second set of terminals provided on the conductive printed board.

* * * * *